(12) United States Patent
Satoh (10) Patent No.: US 8,444,567 B2
(45) Date of Patent: May 21, 2013

(54) ULTRASONIC DIAGNOSTIC APPARATUS FOR REDUCING AN INFLUENCE OF UNEVEN ROTATION OF A FLEXIBLE SHAFT

(75) Inventor: Yoshiaki Satoh, Kaisei-machi (JP)

(73) Assignee: Fujifilm Corporation, Tokyo (JP)

( * ) Notice: Subject to any disclaimer, the term of this patent is extended or adjusted under 35 U.S.C. 154(b) by 289 days.

(21) Appl. No.: 12/801,149

(22) Filed: May 25, 2010

(65) Prior Publication Data

US 2010/0312109 A1 Dec. 9, 2010

(30) Foreign Application Priority Data

Jun. 3, 2009 (JP) ................................. 2009-134458

(51) Int. Cl.
*A61B 8/14* (2006.01)
*G06K 9/00* (2006.01)
*G01H 17/00* (2006.01)

(52) U.S. Cl.
USPC ........... 600/463; 600/466; 600/467; 600/462; 382/128; 73/570

(58) Field of Classification Search
USPC ...... 600/467, 462, 463, 466; 382/128; 73/570
See application file for complete search history.

(56) References Cited

U.S. PATENT DOCUMENTS

| | | | | |
|---|---|---|---|---|
| 5,522,392 A | * | 6/1996 | Suorsa et al. | 600/454 |
| 5,699,806 A | * | 12/1997 | Webb et al. | 600/462 |
| 5,921,934 A | * | 7/1999 | Teo | 600/468 |
| 5,989,191 A | * | 11/1999 | Scampini | 600/453 |
| 6,132,380 A | * | 10/2000 | Cohen et al. | 600/481 |
| 2008/0097208 A1 | * | 4/2008 | Misono | 600/443 |

FOREIGN PATENT DOCUMENTS

| | | |
|---|---|---|
| JP | 10-248844 | 9/1998 |
| JP | 2005-270149 | 10/2005 |

OTHER PUBLICATIONS

Saijo et al., Tissue velocity imaging of coronary artery by rotating-type intravascular ultrasound, Ultrasonics, vol. 42, Issues 1-9, Apr. 2004, pp. 753-757.*

\* cited by examiner

*Primary Examiner* — Michael Rozanski
*Assistant Examiner* — Helene Bor
(74) *Attorney, Agent, or Firm* — Jean C. Edwards, Esq.; Edwards Neils PLLC (57) ABSTRACT

In an ultrasonic diagnostic apparatus using an ultrasonic probe of a mechanical radial scanning type for intracavity observation, stable Doppler mode images with respect to an ROI or a gate position can be generated by reducing an influence of uneven rotation of a flexible shaft. The apparatus includes: a signal processing unit for performing orthogonal detection processing or orthogonal sampling processing on a reception signal to generate a complex baseband signal; a memory for storing the complex baseband signal for at least two frames generated based on ultrasonic echoes received along plural lines; a line selecting unit for selecting one line in each frame from among the plural lines based on the complex baseband signal; and an image signal generating unit for generating an image signal representing information on blood flow based on the complex baseband signal with reference to the line selected in each frame.

5 Claims, 12 Drawing Sheets

ULTRASONIC DIAGNOSTIC APPARATUS FOR REDUCING AN INFLUENCE OF UNEVEN ROTATION OF A FLEXIBLE SHAFT

CROSS-REFERENCE TO RELATED APPLICATION

The present application claims priority from Japanese Patent Application No. 2009-134458 filed on Jun. 3, 2009, the contents of which are incorporated herein by reference in their entirety.

BACKGROUND OF THE INVENTION

1. Field of the Invention

The present invention relates to an ultrasonic diagnostic apparatus using an ultrasonic probe of a mechanical radial scanning type for intracavity observation, and relates to a signal processing program to be used in the ultrasonic diagnostic apparatus.

2. Description of a Related Art

In medical fields, various imaging technologies have been developed for observation and diagnoses within an object to be inspected. Especially, ultrasonic imaging for acquiring interior information of the object by transmitting and receiving ultrasonic waves enables image observation in real time and provides no exposure to radiation unlike other medical image technologies such as X-ray photography or RI (radio isotope) scintillation camera. Accordingly, ultrasonic imaging is utilized as an imaging technology at a high level of safety in a wide range of departments including not only the fetal diagnosis in obstetrics, but also gynecology, circulatory system, digestive system, and so on.

The principle of ultrasonic imaging is as follows. Ultrasonic waves are reflected at a boundary between regions having different acoustic impedances such as a boundary between structures within the object. Therefore, by transmitting ultrasonic beams into the object such as a human body, receiving ultrasonic echoes generated within the object, and obtaining reflection points where the ultrasonic echoes are generated and reflection intensity, outlines of structures (e.g., internal organs, diseased tissues, and so on) existing within the object can be extracted.

Further, an ultrasonic endoscope for obtaining ultrasonic diagnostic images by performing scanning within a body cavity by using ultrasonic waves has been conventionally proposed. In the ultrasonic endoscope, an electronic scanning system has been recently proposed against a conventional mechanical scanning system. The electronic scanning system can perform scanning with a higher degree of freedom than the mechanical scanning system and can realize a Doppler mode (including a CF (color flow) mode and a PW (pulse wave) mode) in addition to a B (brightness) mode, and is becoming predominant.

Here, the B-mode refers to a mode of converting amplitudes of ultrasonic echoes into brightness and displaying a two-dimensional tomographic image. Further, the CF mode refers to a mode of mapping average blood flow velocities, flow fluctuation, intensity of flow signals, flow power, or the like in various colors and superimposing it on the B-mode image, and the PW mode refers to a mode of displaying velocities of ultrasonic echo sources detected based on transmission and reception of pulse waves.

Furthermore, as a device similar to the ultrasonic endoscope, there is an ultrasonic probe to be inserted into a forceps hole of the endoscope. However, since the ultrasonic probe has a thin diameter, only the mechanical radial scanning system is realized. In the mechanical radial scanning system, a displayed image often rotates due to uneven rotation (jitter) of a flexible shaft for rotating ultrasonic transducers. Especially, in the Doppler mode, there has been a problem that a displayed image (object) rotates relative to an ROI (region of interest) or a gate position to be set, and a region really desired to be observed is out of a field of view.

As a related technology, Japanese Patent Application Publication JP-P2005-270149A discloses an apparatus that can perform a quantitative image diagnosis within a cardiac blood vessel (coronary vessel) in a short time (in real time) at low cost. The apparatus is an apparatus for obtaining a tomographic image of a blood vessel based on reflected waves (ultrasonic echoes) of an ultrasonic beam radiated from an ultrasonic probe provided in a catheter inserted into the blood vessel, and includes (1) means for irradiating entire circumference of the vessel wall while rotating the ultrasonic probe, observing ultrasonic echoes from the vessel wall, and analyzing a Doppler shift frequency as a difference between a frequency of the irradiating ultrasonic beam and a frequency of the ultrasonic echoes, i.e., an amount of shift change produced due to a Doppler effect, (2) means for removing an influence of movement of the catheter center due to the influence of pulsation by adding a Doppler shift frequency in a certain irradiation direction and a Doppler shift frequency observed in a direction at 180 degrees from that direction to each other in order to remove a Doppler shift frequency depending on the movement of the catheter center from the Doppler shift frequency, and handling only the Doppler shift frequency from the vessel wall, and (3) means for digitizing an ultrasonic frequency by A/D conversion and analyzing it by using a computer image information processing unit in order to compute a tomographic image of the blood vessel based on the Doppler shift frequency by the vessel wall, and displaying a structure of the vessel wall as an image.

That is, JP-P2005-270149A proposes a method of canceling fluctuation of the ultrasonic probe center position when the Doppler shift amount is observed in the Doppler mode. However, the method cannot deal with the case where the observed region rotates.

Further, Japanese Patent Application Publication JP-A-10-248844 discloses an ultrasonic image diagnostic apparatus that can obtain image data without reduction of the field of view of an ultrasonic tomographic image and without rotation of image even when image shift occurs, and thereby, construct an accurate three-dimensional image without distortion. The ultrasonic image diagnostic apparatus includes an ultrasonic probe for obtaining three-dimensional image data including continuous plural ultrasonic tomographic images, rotating means for performing rotation processing on a first ultrasonic tomographic image among the plural ultrasonic tomographic images, and correlation computing means for performing correlation computation of the first ultrasonic tomographic image rotation-processed by the rotating means and a second ultrasonic tomographic image among the plural ultrasonic tomographic images to output a correlation value, wherein the rotating means performs rotation processing again on the first ultrasonic tomographic image by an angle at which the correlation value computed by the correlation computing means is the highest.

The ultrasonic image diagnostic apparatus according to JP-A-10-248844 obtains an amount of rotation from the correlation value of the image data representing continuous plural images in three-dimensional display of a B-mode image, and performs polar coordinate conversion for correcting the angle shift to obtain a corrected three-dimensional image. However, there is no consideration to the Doppler mode requiring real time operation.

SUMMARY OF THE INVENTION

The present invention has been achieved in view of the above-mentioned points. A purpose of the present invention is, in an ultrasonic diagnostic apparatus using an ultrasonic probe of a mechanical radial scanning type for intracavity observation such as an ultrasonic probe to be inserted into a forceps hole of an endoscope, to generate stable Doppler mode images with respect to an ROI (region of interest) or a gate position to be set by reducing an influence of uneven rotation (jitter) of a flexible shaft.

In order to accomplish the above-mentioned purpose, an ultrasonic diagnostic apparatus according to one aspect of the present invention is an ultrasonic diagnostic apparatus using an ultrasonic probe of a mechanical radial scanning type for intracavity observation and including an ultrasonic transducer for transmitting ultrasonic waves and receiving ultrasonic echoes, and the apparatus includes: a signal processing unit for performing orthogonal detection processing or orthogonal sampling processing on a reception signal outputted from the ultrasonic transducer to generate a complex baseband signal; a memory for storing the complex baseband signal for at least two frames generated based on the ultrasonic echoes received along plural lines when the ultrasonic transducer rotates; a line selecting unit for selecting one line in each frame from among the plural lines based on the complex baseband signal stored in the memory; and an image signal generating unit for generating an image signal representing information on blood flow based on the complex baseband signal with reference to the line selected in each frame by the line selecting unit.

Further, a signal processing program according to one aspect of the present invention is a signal processing program, embodied in non-transitory form on a computer readable medium comprising one of a built-in hard disk, a flexible disk, an MO, an MT, a RAM, a CD-ROM, and a DVD-ROM, for processing a complex baseband signal generated by performing orthogonal detection processing or orthogonal sampling processing on a reception signal outputted from an ultrasonic transducer for transmitting ultrasonic waves and receiving ultrasonic echoes in an ultrasonic diagnostic apparatus using an ultrasonic probe of a mechanical radial scanning type for intracavity observation, and the program allows a CPU to execute the procedures of: (a) selecting a line in a first frame and selecting, in a second frame subsequent to the first frame, a line corresponding to the complex baseband signal having the highest correlation with the complex baseband signal corresponding to the line selected in the first frame, based on the complex baseband signal for at least two frames generated based on the ultrasonic echoes received along plural lines when the ultrasonic transducer rotates; and (b) generating an image signal representing information on blood flow based on the complex baseband signal with reference to the line selected in each frame at procedure (a).

According to the one aspect of the present invention, by generating an image signal representing information on blood flow based on the complex baseband signal with reference to one line selected in each frame based on the complex baseband signal, stable Doppler mode images with respect to an ROI or a gate position to be set can be generated by reducing an influence of uneven rotation (jitter) of a flexible shaft.

DESCRIPTION OF THE PREFERRED EMBODIMENTS

Hereinafter, embodiments of the present invention will be explained in detail with reference to the drawings. The same signs are assigned to the same component elements and the explanation thereof will be omitted.

Figure 1:
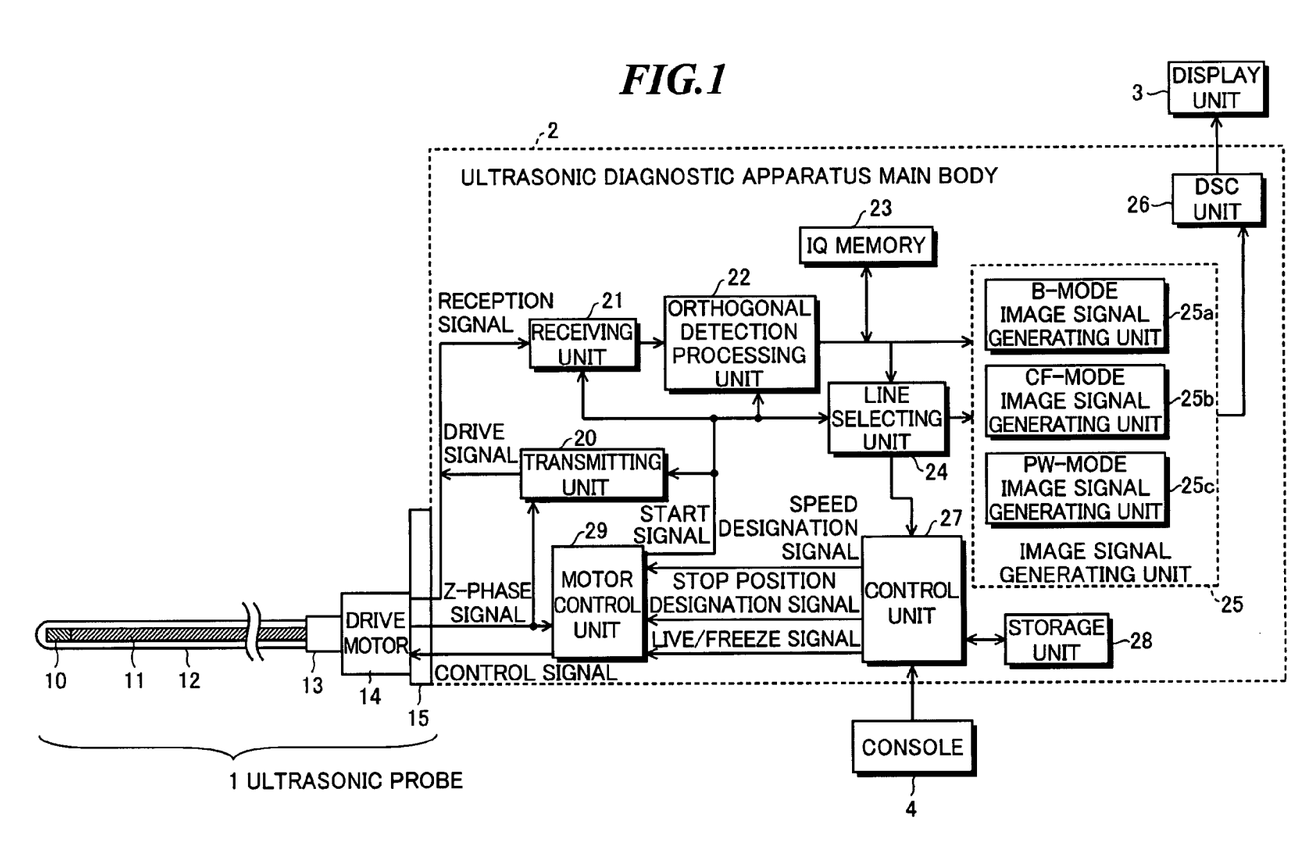
FIG. 1 is a block diagram showing a configuration of an ultrasonic diagnostic apparatus according to one embodiment of the present invention.

FIG. 1 is a block diagram showing a configuration of an ultrasonic diagnostic apparatus according to one embodiment of the present invention. As shown in FIG. 1, the ultrasonic diagnostic apparatus includes an ultrasonic probe 1, an ultrasonic diagnostic apparatus main body 2, a display unit 3, and a console 4.

The ultrasonic probe 1 is an ultrasonic probe of a mechanical radial scanning type for intracavity observation, and in the embodiment, an ultrasonic probe to be inserted into a forceps hole of an endoscope will be explained as an example. As shown in FIG. 1, the ultrasonic probe 1 includes an ultrasonic transducer 10, a rotation transmission cable 11, a protective cover 12, a supporting part 13, a drive motor 14, and a connector part 15.

The ultrasonic transducer 10 transmits ultrasonic waves according to an applied drive signal, and receives propagating ultrasonic echoes to output a reception signal. The ultrasonic transducer 10 includes a vibrator having electrodes formed on both ends of a material having a piezoelectric property (piezoelectric material) such as a piezoelectric ceramic represented by PZT (Pb (lead) zirconate titanate), a polymeric piezoelectric element represented by PVDF (polyvinylidene difluoride), or the like.

When a pulsed or continuous wave voltage is applied to the electrodes of the vibrator, the piezoelectric material expands and contracts. By the expansion and contraction, pulse or continuous wave ultrasonic waves are generated from the vibrator. Further, the vibrator expands and contracts by receiving the propagating ultrasonic waves to generate an electric signal. The electric signal is outputted as a reception signal of ultrasonic waves.

The rotation transmission cable 11 includes a flexible shaft, and transmits the rotational force generated by the drive motor 14 to the ultrasonic transducer 10. Further, the rotation transmission cable 11 transfers a drive signal generated in the ultrasonic diagnostic apparatus main body 2 to the ultrasonic transducer 10, and transfers a reception signal outputted from the ultrasonic transducer 10 to the ultrasonic diagnostic apparatus main body 2. One end of the protective cover 12 for covering and protecting the ultrasonic transducer 10 and the rotation transmission cable 11 is supported by the supporting part 13, and the other end is inserted into the forceps hole of the endoscope.

The drive motor 14 is a motor in which the rotational speed and the stop position can be controlled, and rotates the ultrasonic transducer 10 according to a control signal supplied from the ultrasonic diagnostic apparatus main body 2, and outputs one pulse (a Z-phase signal) per rotation. The connector part 15 is used for attaching the ultrasonic probe 1 to the ultrasonic diagnostic apparatus main body 2.

The ultrasonic diagnostic apparatus main body 2 includes a transmitting unit 20, a receiving unit 21, an orthogonal detection processing unit 22, an IQ memory 23, a line selecting unit 24, an image signal generating unit 25, a DSC unit 26, a control unit 27, a storage unit 28, and a motor control unit 29. The transmitting unit 20 includes a pulser, for example, and generates a drive signal having high-voltage pulses and supplies the generated drive signal to the ultrasonic transducer 10.

The receiving unit 21 includes a preamplifier, and amplifies a reception signal (RF signal) outputted from the ultrasonic transducer 10. The orthogonal detection processing unit 22 performs orthogonal detection processing or orthogonal sampling processing on the reception signal outputted from the receiving unit 21 to generate a complex baseband signal (I-signal and Q-signal). Here, the receiving unit 21 and the orthogonal detection processing unit 22 correspond to a signal processing unit for performing orthogonal detection processing or orthogonal sampling processing on the reception signal outputted from the ultrasonic transducer 10 to generate a complex baseband signal.

Figure 2:
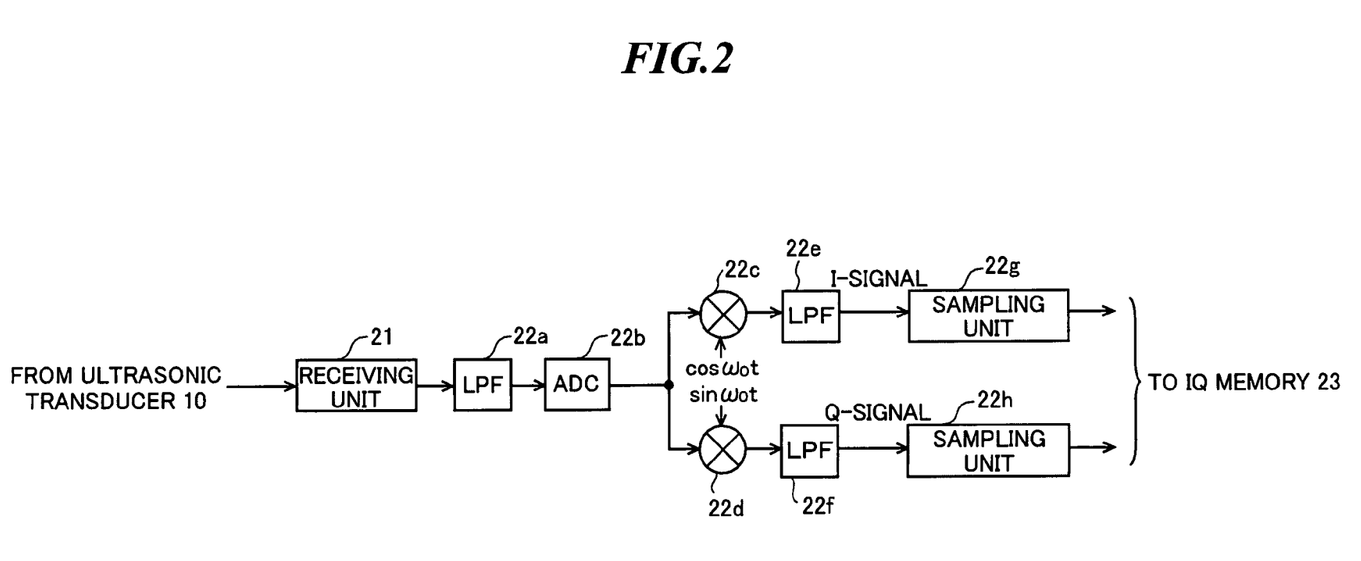
FIG. 2 shows a first configuration example of a signal processing unit of the ultrasonic diagnostic apparatus as shown in FIG. 1.

FIG. 2 shows a first configuration example of the signal processing unit of the ultrasonic diagnostic apparatus as shown in FIG. 1. As shown in FIG. 2, the signal processing unit includes the receiving unit 21, a low-pass filter (LPF) 22a, an analog/digital converter (ADC) 22b, mixers (multiplication circuits) 22c and 22d, low-pass filters (LPFs) 22e and 22f, and sampling units 22g and 22h.

The LPF 22a limits the band of the reception signal outputted from the receiving unit 21 to prevent aliasing in A/D conversion. The ADC 22b converts the analog reception signal outputted from the LPF 22a into a digital reception signal. The digital reception signal generated by the ADC 22b is input to the mixers 22c and 22d.

The mixer 22c multiplies the reception signal, that has been converted into the digital signal by the ADC 22b, by a local oscillation signal $\cos \omega_0 t$, and the LPF 22e performs low-pass filter processing on the signal outputted from the mixer 22c, and thereby, an I-signal representing a real number component is generated. On the other hand, the mixer 22d multiplies the reception signal, that has been converted into the digital signal by the ADC 22b, by a local oscillation signal $\sin \omega_0 t$, which is obtained by rotating the phase of the local oscillation signal $\cos \omega_0 t$ by $\pi/2$, and the LPF 22f performs low-pass filter processing on the signal outputted from the mixer 22d, and thereby, a Q-signal representing an imaginary number component is generated.

The sampling units 22g and 22h sample (resample) the I-signal and the Q-signal, respectively. The sampled I-signal and Q-signal are supplied to the IQ memory 23. In the embodiment, orthogonal detection processing is performed on the reception signal to drop the frequency range of the reception signal to the baseband frequency range, and the complex baseband signal is stored in the IQ memory 23, and thereby, the memory capacity is reduced.

Figure 3A:
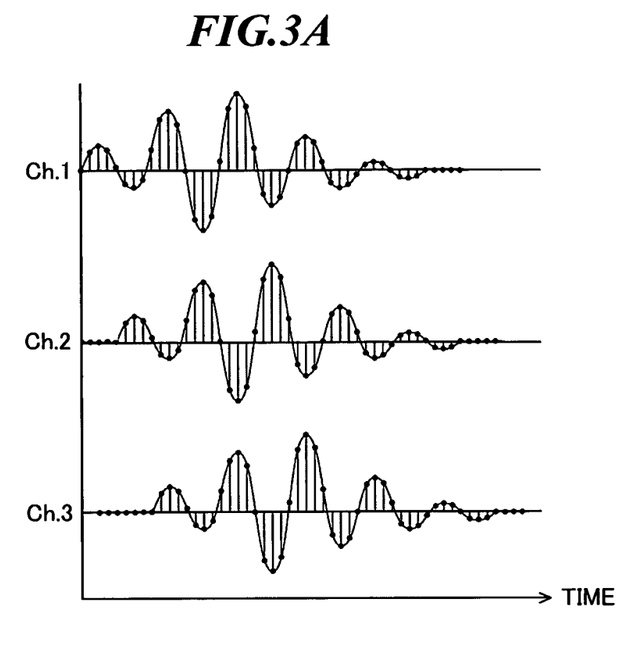
FIGS. 3A and 3B are waveform charts showing sampling by an ADC as shown in FIG. 2 and sampling by a sampling unit in comparison.
Figure 3B:
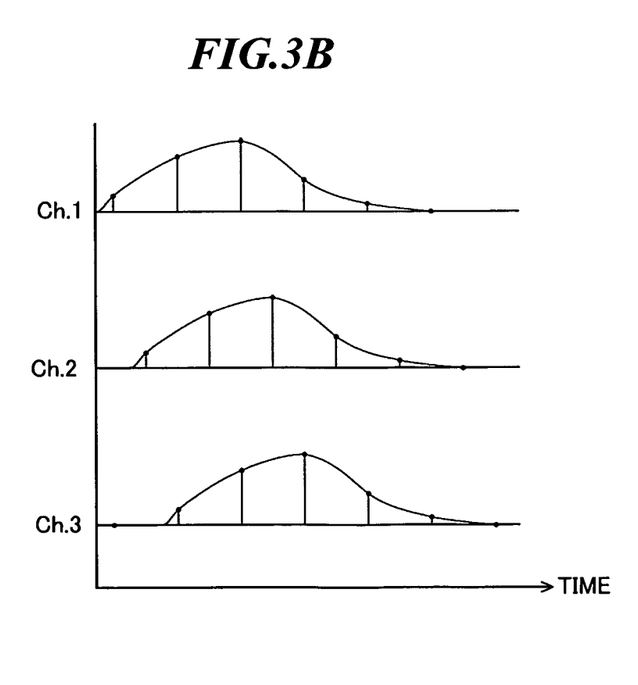

FIGS. 3A and 3B are waveform charts showing sampling by the ADC as shown in FIG. 2 and sampling by the sampling unit in comparison. FIG. 3A shows sampling by the ADC 22b with respect to three channels Ch. 1 to Ch. 3, and FIG. 3B shows sampling by the sampling unit 22g with respect to three channels Ch. 1 to Ch. 3. Compared to the case where the RF signal is sampled as shown in FIG. 3A and sample data is transferred, the data volume can significantly be reduced by sampling the baseband signal as shown in FIG. 3B.

Figure 4:
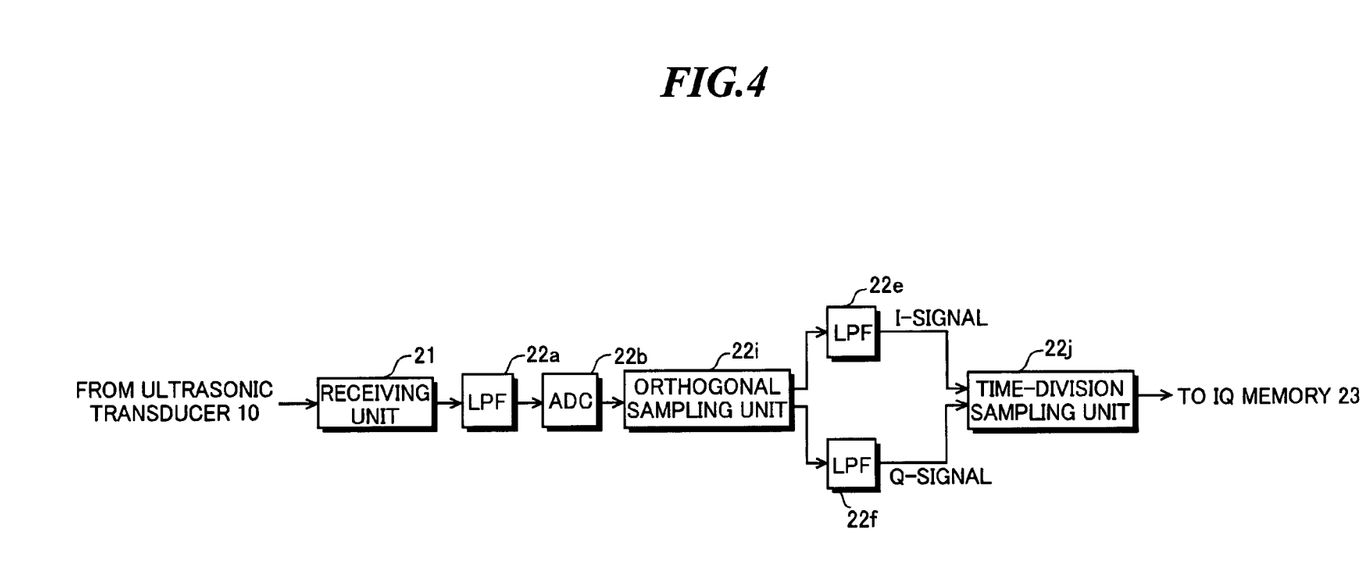
FIG. 4 shows a second configuration example of a signal processing unit of the ultrasonic diagnostic apparatus as shown in FIG. 1.

FIG. 4 shows a second configuration example of the signal processing unit of the ultrasonic diagnostic apparatus as shown in FIG. 1. In the second configuration example as shown in FIG. 4, an orthogonal sampling unit 22i is provided in place of the mixers 22c and 22d, and a time-division sampling unit 22j is provided in place of the sampling units 22g and 22h in the first configuration example as shown in FIG. 2.

Figure 5:
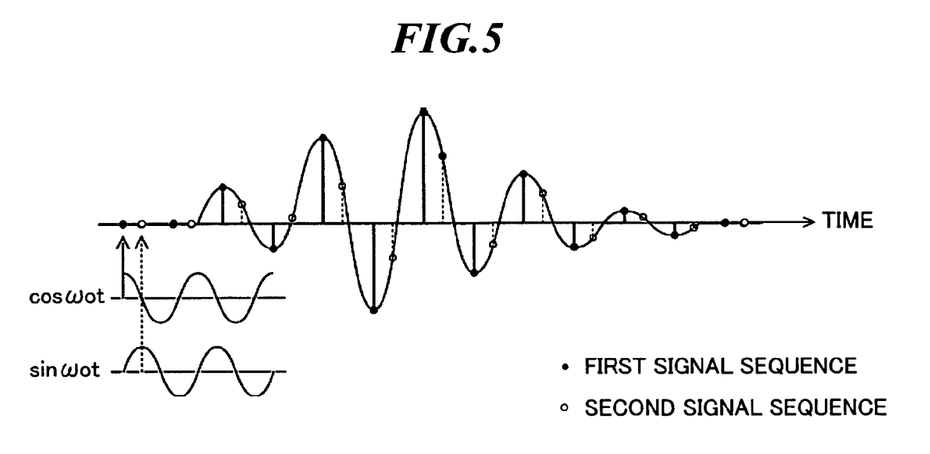
FIG. 5 is a waveform chart for explanation of an operation of an orthogonal sampling unit as shown in FIG. 4.

FIG. 5 is a waveform chart for explanation of an operation of the orthogonal sampling unit as shown in FIG. 4. The orthogonal sampling unit 22i generates a first signal sequence by sampling the reception signal that has been converted into a digital signal by the ADC 22b in synchronization with the phase of $\cos \omega_0 t$, and generates a second signal sequence by sampling the reception signal in synchronization with the phase of $\sin \omega_0 t$.

Referring to FIG. 4 again, the LPF 22e performs low-pass filter processing on the first signal sequence outputted from the orthogonal sampling unit 22i to generate an I-signal representing a real number component, and the LPF 22f performs low-pass filter processing on the second signal sequence outputted from the orthogonal sampling unit 22i to generate a Q-signal representing an imaginary number component. Thereby, the mixers 22c and 22d as shown in FIG. 2 may be omitted.

The time-division sampling unit 22j alternately and time-divisionally samples (resamples) the I-signal and the Q-signal. For example, the time-division sampling unit 22j samples the I-signal in synchronization with the phase of $\cos \omega_0 t$, and samples the Q-signal in synchronization with the phase of $\sin \omega_0 t$. The sampled I-signal and Q-signal are supplied to the IQ memory 23.

In the above-mentioned configuration, the mixers 22c and 22d, the LPF 22e and 22f, the sampling units 22g and 22h, the orthogonal sampling unit 22i, and the time-division sampling unit 22j may be formed of digital circuits, or formed of a central processing unit (CPU) and software (program) for allowing the CPU to perform various kinds of processing. Alternatively, the mixers 22c and 22d and the LPFs 22e and 22f may be formed of analog circuits, and the ADC 22b may be omitted. In this case, A/D conversion of the complex baseband signal is performed by the sampling units 22g and 22h or the time-division sampling unit 22j.

Referring to FIG. 1 again, the IQ memory 23 sequentially stores the complex baseband signal (I-signal and Q-signal) at least in units of two frames, which is continuously generated based on ultrasonic echoes received along plural lines when the ultrasonic transducer 10 rotates, in accordance with corresponding line numbers. The line selecting unit 24 selects one line in each frame from among the plural lines based on the complex baseband signal stored in the IQ memory 23.

The image signal generating unit 25 includes a B-mode image signal generating unit 25a, a CF mode image signal generating unit 25b, and a PW mode image signal generating unit 25c. The B-mode image signal generating unit 25a performs processing such as logarithmic compression or amplitude computation on the complex baseband signal corresponding to the plural lines and read out from the IQ memory 23 with reference to the line selected in each frame by the line selecting unit 24, and thereby, generates a B-mode image signal representing a B-mode image as tomographic image information on tissues within the object.

The CF mode image signal generating unit 25b performs autocorrelation processing on the complex baseband signal corresponding to the plural lines and read out from the IQ memory 23 with reference to the line selected in each frame by the line selecting unit 24 to generate an image signal representing information on the blood flow, and superimposing the image signal on the B-mode image signal generated by the B-mode image signal generating unit 25a, and thereby, generates a CF mode image signal representing a CF mode image in which the information on the blood flow is displayed as a color image superimposed on the B-mode image.

With reference to the line selected in each frame by the line selecting unit 24, the PW mode image signal generating unit 25c performs the FFT (fast Fourier transform) processing on the complex baseband signal corresponding to the line and read out from the IQ memory 23, and thereby, generates a PW mode image signal representing an PW mode image in which a velocity of the blood flow detected based on transmission and reception of pulse waves is displayed. Each of the CF mode and the PW mode is one form of the Doppler mode for obtaining information on blood flow (movement condition, moving velocity, and so on) by utilizing the Doppler phenomenon.

The DSC unit 26 converts (raster-converts) the image signals generated by the image signal generating unit 25 into image signals that follow the normal scan system of television signals, and performs necessary image processing such as gradation processing and D/A conversion to generate image signals for display. The display unit 3 includes a display device such as an LCD, and displays ultrasonic diagnostic images based on the image signals for display generated by the DSC unit 26.

The control unit 27 controls the respective units of the ultrasonic diagnostic apparatus main body 2 according to the operation of an operator using the console 4. Further, the control unit 27 supplies a speed designation signal for designating the rotational speed of the ultrasonic transducer 10, a stop position designation signal for designating the stop position of the ultrasonic transducer 10, and a live/freeze signal for switching between a live mode and a freeze mode to the motor control unit 29. Here, the live mode refers to a mode of displaying a moving image based on the reception signal subsequently obtained by transmission and reception of ultrasonic waves, and the freeze mode refers to a mode of displaying a still image based on the complex baseband signal or the image signal stored in a memory or the like.

The motor control unit 29 supplies control signals to the drive motor 14 under the control of the control unit 27, and thereby, controls the rotational speed and the stop position of the ultrasonic transducer 10. Further, the motor control unit 29 supplies a start signal representing the start of imaging operation to the transmitting unit 20, the receiving unit 21, and so on.

In the embodiment, the line selecting unit 24, the image signal generating unit 25, the DSC unit 26, the control unit 27, and the motor control unit 29 are formed of a control processing unit (CPU) and software (program) for allowing the CPU to perform various kinds of processing. However, they may be formed of digital circuits. The software (program) is stored in the storage unit 28 and embodied in non-transitory form on a computer readable recording medium. As the recording medium in the storage unit 28, not only a built-in hard disk but also a flexible disk, an MO, an MT, a RAM, a CD-ROM, a DVD-ROM, or the like may be used.

Next, an operation of the ultrasonic diagnostic apparatus according to the one embodiment of the present invention will be explained.

Figure 6:
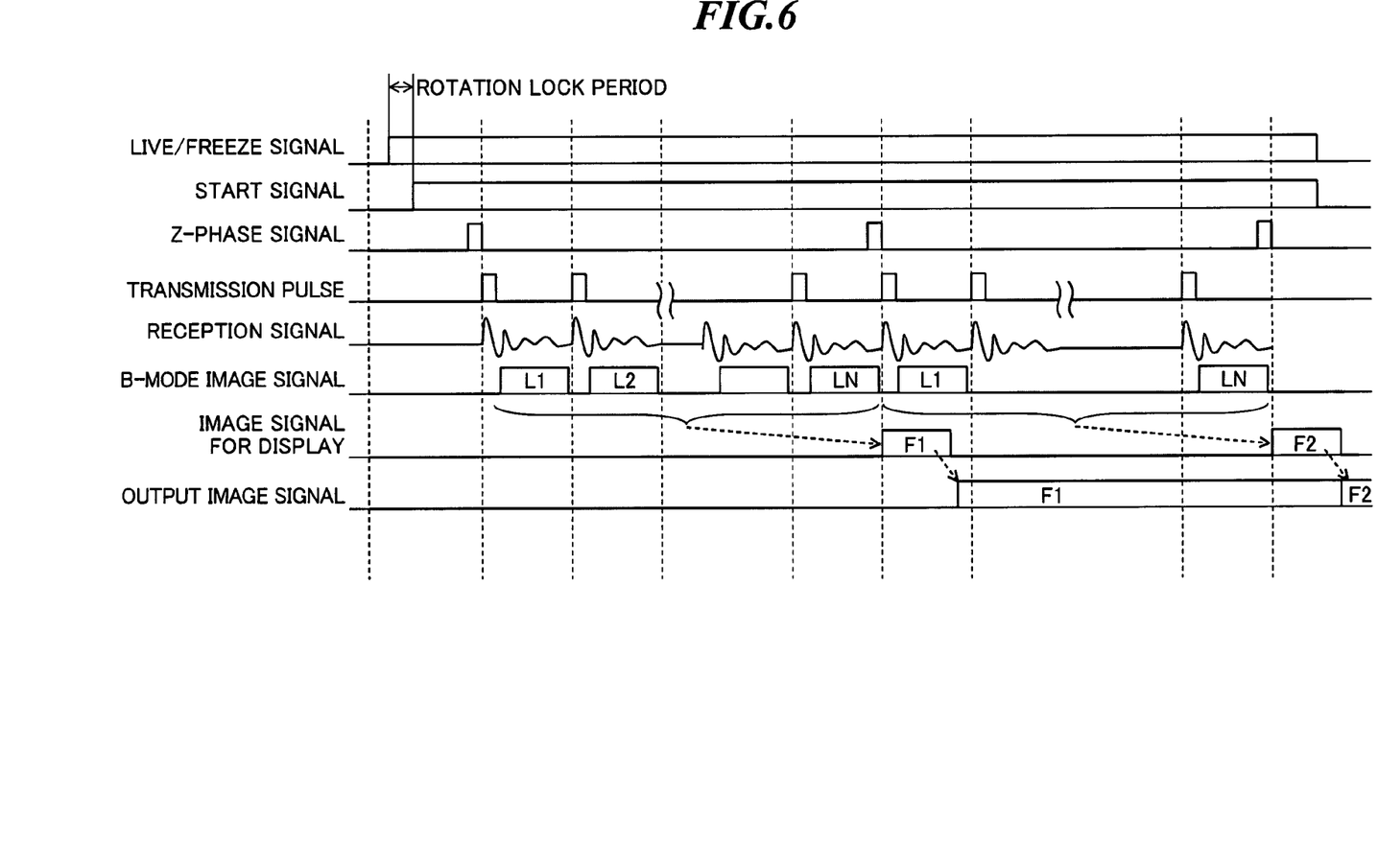
FIG. 6 is a timing chart showing an operation in B-mode of the ultrasonic diagnostic apparatus as shown in FIG. 1.

FIG. 6 is a timing chart showing an operation in B-mode of the ultrasonic diagnostic apparatus as shown in FIG. 1. The control unit 27 sets the live mode by activating the live/freeze signal to the high level according to the operation of an operator using the console 4. Then, after a predetermined rotation lock period elapses, the motor control unit 29 activates the start signal to the high level and allows the drive motor 14 to start rotational movement.

When starting the rotational movement, the drive motor 14 generates one pulse for one rotation as a Z-phase signal. The transmitting unit 20 generates a drive signal at timings obtained by dividing the pulse period of the Z-phase signal into equal intervals, and thereby, the ultrasonic transducer 10 sequentially transmits plural transmission pulses to the object along the plural lines while rotating. Further, the ultrasonic transducer 10 sequentially receives ultrasonic echoes reflected from the object along the plural lines to output a reception signal.

The orthogonal detection processing unit 22 generates a complex baseband signal based on the reception signal, and the B-mode image signal generating unit 25a generates a B-mode image signal including plural lines L1, L2, . . . , LN in each frame based on the complex baseband signal. The DSC unit 26 generates an image signal for display including plural frames F1, F2, . . . based on the B-mode image signal, and D/A-converts the image signal for display and outputs an analog signal.

Figure 7:
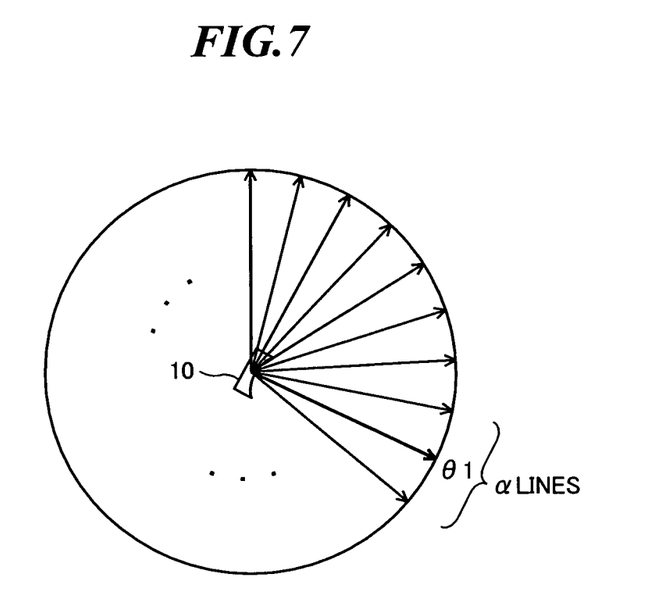
FIG. 7 is a diagram for explanation of an operation of a line selecting unit of the ultrasonic diagnostic apparatus as shown in FIG. 1.

FIG. 7 is a diagram for explanation of an operation of the line selecting unit of the ultrasonic diagnostic apparatus as shown in FIG. 1. As shown in FIG. 7, the ultrasonic transducer 10 sequentially generates plural transmission pulses along the plural lines while rotating, and sequentially receives ultrasonic echoes reflected from the object along the plural lines. Here, the line selecting unit 24 selects one line from α lines (α is an integer number equal to or more than two).

Figure 8:
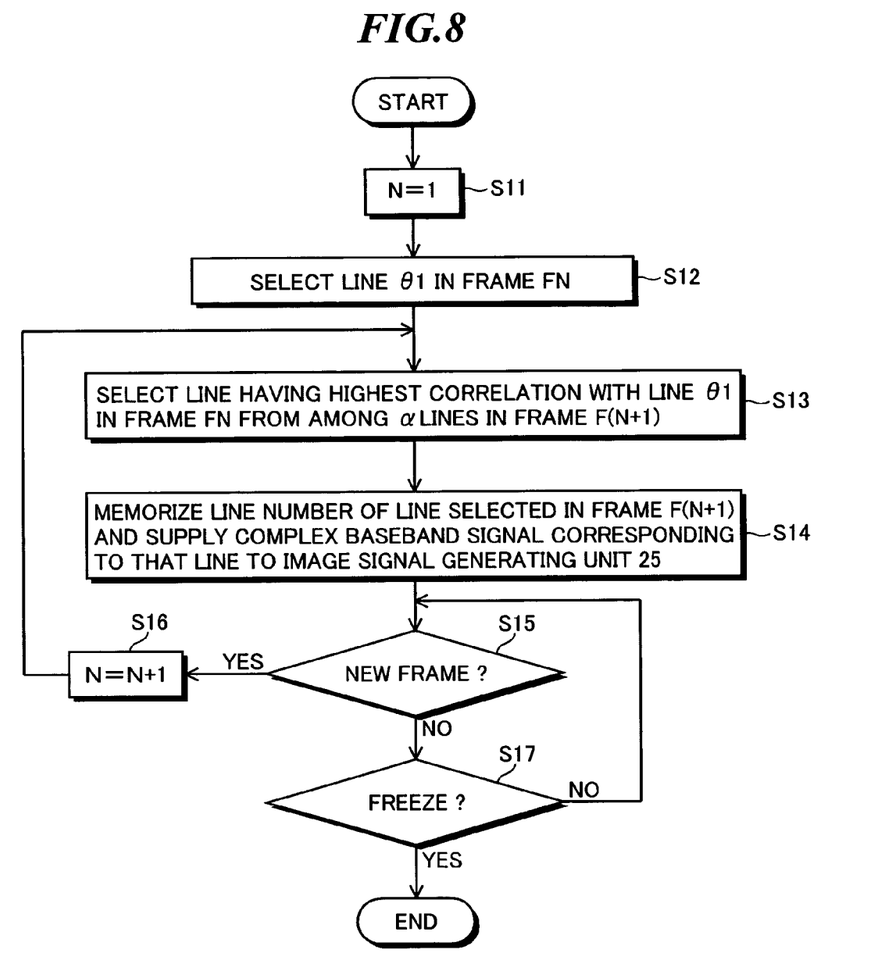
FIG. 8 is a flowchart showing the operation of the line selecting unit of the ultrasonic diagnostic apparatus as shown in FIG. 1.

FIG. 8 is a flowchart showing the operation of the line selecting unit of the ultrasonic diagnostic apparatus as shown in FIG. 1. In the embodiment, a signal processing program stored in the storage unit 28 allows the CPU to execute the following steps (procedures). First, a complex baseband signal for at least two frames F1 and F2 is stored in the IQ memory 23.

At step S1as shown in FIG. 8, a value of "N" is initially set to "1". At step S12, the line selecting unit 24 selects line θ1 located substantially the center of the ROI (region of interest) set by the operator.

At step S13, the line selecting unit 24 selects a line having the highest correlation with the line θ1 in the frame FN from among the α lines in the frame F(N+1) and uses the line as new line θ1. That is, in the frame F(N+1), the line selecting unit 24 selects a line corresponding to the complex baseband signal having the highest correlation with the complex baseband signal corresponding to the line θ1 selected in the frame FN.

Here, as a method of obtaining correlation of the complex baseband signal between two lines, the following method may be cited. For example, a correlation coefficient CI of the I-signal is obtained between two lines and a correlation coefficient CQ of the Q-signal is obtained between the two lines, and a determination is made that the lines, in which an average value C=(CI+CQ)/2 of the correlation coefficient CI and the correlation coefficient CQ is the maximum, have the highest correlation. Alternatively, errors EI1, EI2, . . . of the I-signal are obtained between two lines and errors EQ1, EQ2, . . . of the Q-signal are obtained between two lines, and a determination is made that the lines, in which a sum of squares of the errors $E=EI1^2+EI2^2+ \ldots +EQ1^2+EQ2^2+ \ldots$ is the minimum, have the highest correlation.

At step S14, the line selecting unit 24 memorizes the line number of the line selected in the frame F(N+1), and supplies the complex baseband signal corresponding to that line to the image signal generating unit 25. The image signal generating unit 25 generates an image signal representing information on blood flow based on the complex baseband signal corresponding to the line selected in each frame.

At step S15, the line selecting unit 24 determines whether the complex baseband signal for a new frame has been stored in the IQ memory 23 or not. If the complex baseband signal for a new frame has been stored in the IQ memory 23, the process moves to step S16, otherwise the process moves to step S17.

At step S16, the value of "N" is incremented by "1" and the process returns to step S13. Thereby, the processing at steps S13 and S14 is repeated. On the other hand, at step S17, whether the freeze mode has been set or not is determined. If the freeze mode has not been set, the process returns to step S15, and if the freeze mode has been set, the process ends.

Alternatively, at step S13, the line selecting unit 24 may compare phase information in the complex baseband signal generated based on the ultrasonic echoes received along the plural lines from a predetermined depth within the object when the ultrasonic transducer 10 rotates, and thereby, select a line closest in a phase to the line θ1 in the frame FN from among the α lines in the frame F(N+1) and uses the line as new line θ1. That is, the line selecting unit 24 selects, in the frame F(N+1), a line corresponding to the complex baseband signal closest in a phase to the complex baseband signal corresponding to the line 81 selected in the frame FN.

Here, given that the amplitude of the complex baseband signal is "A" and the phase is "θ", then the I-signal and the Q-signal are expressed as below.

$I = A\cos\theta$ $Q = A\sin\theta$

From them, the amplitude "A" is obtained as fallows.

$A = (I^2 Q^2)^{1/2}$

Further, the phase "θ" is obtained as fallows.

$Q/I = \tan\theta$ $\theta = a\tan(Q/I)$

In the above description, attention is focused on one line, but a correlation value or a phase may be obtained by using information on one area in place of one line. In this case, the influence of uneven rotation of the flexible shaft can be corrected more accurately.

Figure 9:
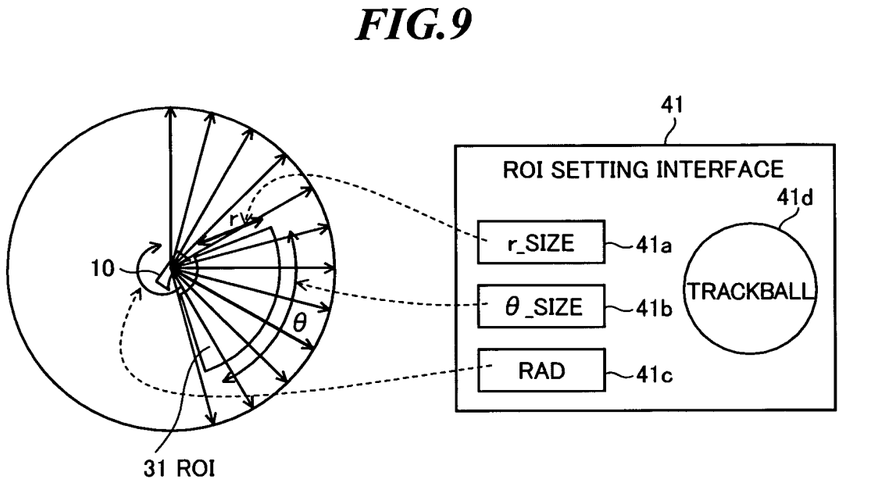
FIG. 9 is a diagram for explanation of setting of an ROI in CF mode.

FIG. 9 is a diagram for explanation of setting of the ROI in the CF mode. On the console 4 of the ultrasonic diagnostic apparatus as shown in FIG. 1, an ROI setting interface 41 as shown in FIG. 9 is provided. The ROI setting interface 41 is provided with an ROI radius size setting button 41a for setting the size of the ROI in the radius "r" direction, an ROI angle size setting button 41b for setting the size of the ROI in the angle "θ" direction, an ROI position setting button 41c for setting the position of the ROI, and a trackball 41d. The operator operates them, and thereby, an ROI 31 is set in an ultrasonic diagnostic image displayed on the display unit 3.

Figure 10:
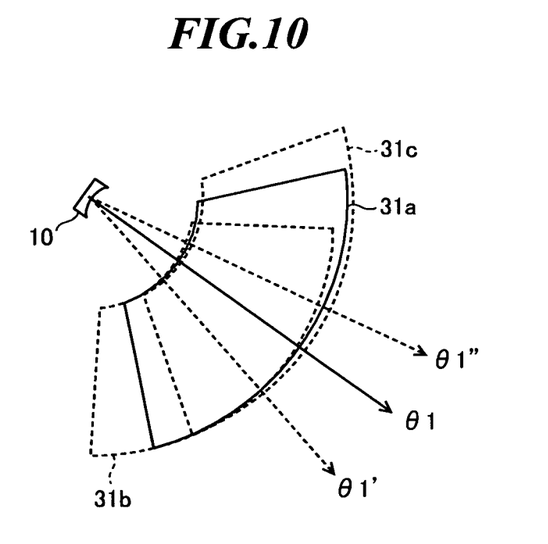
FIG. 10 is a diagram for explanation of reduction of jitter in an ultrasonic diagnostic image as shown in FIG. 1.

FIG. 10 is a diagram for explanation of reduction of jitter in an ultrasonic diagnostic apparatus as shown in FIG. 1. As shown in FIG. 10, the line θ1 in the first frame may be affected by the uneven rotation (jitter) of the flexible shaft and moved to the position of line θ1' or θ1" in the second frame subsequent to the first frame. If an image signal is generated under the condition, an ROI 31a moves to the position of an ROI 31b or 31c. Accordingly, in the embodiment, the line selecting unit 24 selects, in the second frame, a line having the highest correlation with the line θ1 in the first frame, and the image signal generating unit 25 generates an image signal with reference to the line selected by the line selecting unit 24, and thereby, the rotation of the image due to jitter can be prevented.

Figure 11:
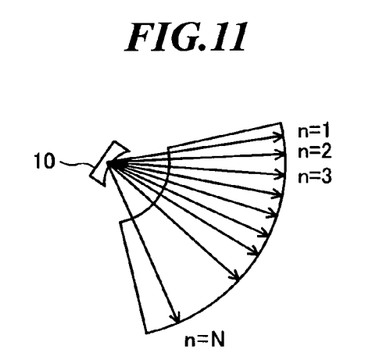
FIG. 11 is a diagram for explanation of an operation of a CF-mode image signal generating unit of the ultrasonic diagnostic apparatus as shown in FIG. 1.

FIG. 11 is a diagram for explanation of an operation of the CF-mode image signal generating unit of the ultrasonic diagnostic apparatus as shown in FIG. 1. As shown in FIG. 11, the ultrasonic transducer 10 sequentially generates plural transmission pulses along the plural lines while rotating, and sequentially receives ultrasonic echoes reflected from the object along the plural lines. In the CF mode, the control unit 27 generates a speed designation signal such that the rotation of the ultrasonic transducer 10 becomes slower than that in the B-mode. Thereby, the CF-mode image signal generating unit 25b regards the ultrasonic echoes obtained in the lines where n=1 to 3 as ultrasonic echoes from the same direction, and obtains autocorrelation of the complex baseband signal obtained based on those ultrasonic echoes.

Figure 12:
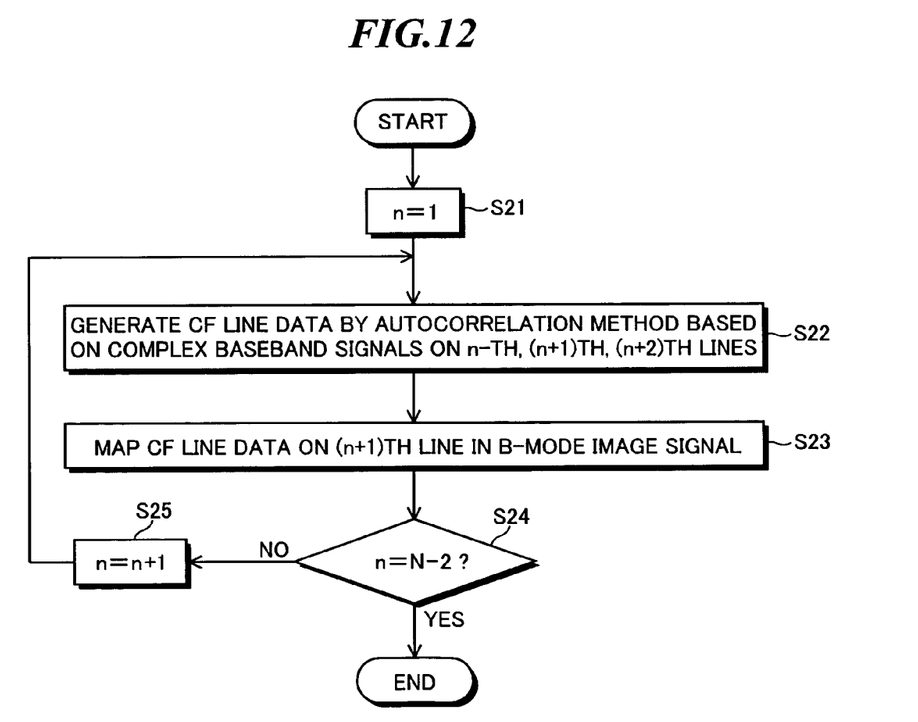
FIG. 12 is a flowchart showing the operation of the CF-mode image signal generating unit of the ultrasonic diagnostic apparatus as shown in FIG. 1.

FIG. 12 is a flowchart showing the operation of the CF-mode image signal generating unit of the ultrasonic diagnostic apparatus as shown in FIG. 1. At step S21 as shown in FIG. 12, the value of "n" is initially set to "1". At step S22, the CF-mode image signal generating unit 25b generates CF line data by the autocorrelation method based on the complex baseband signal on the n-th, (n+1) th, (n+2)th lines.

At step S23, the CF-mode image signal generating unit 25b maps the generated CF line data on the (n+1) th line in B-mode image signal generated by the B-mode image signal generating unit 25a.

At step S24, the CF-mode image signal generating unit 25b determines whether the value of "n" is equal to (N−2) or not. If the value of "n" is not equal to (N−2), the process moves to step S25. At step S25, the value of "n" is incremented by "1" and the process returns to step S22. Thereby, the processing at steps S22 and S23 is repeated. If the value of "n" is equal to (N−2), the process ends.

Figure 13:
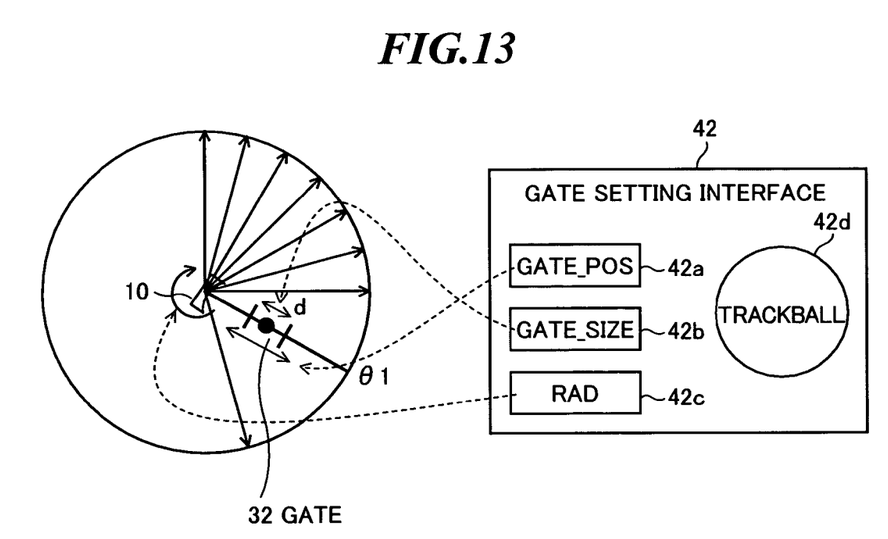
FIG. 13 is a diagram for explanation of setting of an ROI in PW mode.

FIG. 13 is a diagram for explanation of setting of an ROI in the PW mode. On the console 4 of the ultrasonic diagnostic apparatus as shown in FIG. 1, a gate setting interface 42 as shown in FIG. 13 is provided. The gate setting interface 42 is provided with a gate position setting button 42a for setting the position of a gate, a gate size setting button 42b for setting the size (distance "d") of the gate, a gate angle setting button 42c for setting the angle of the gate, and a trackball 42d. The operator operates them, and thereby, a gate 32 is set in an ultrasonic diagnostic image displayed on the display unit 3.

Figure 14:
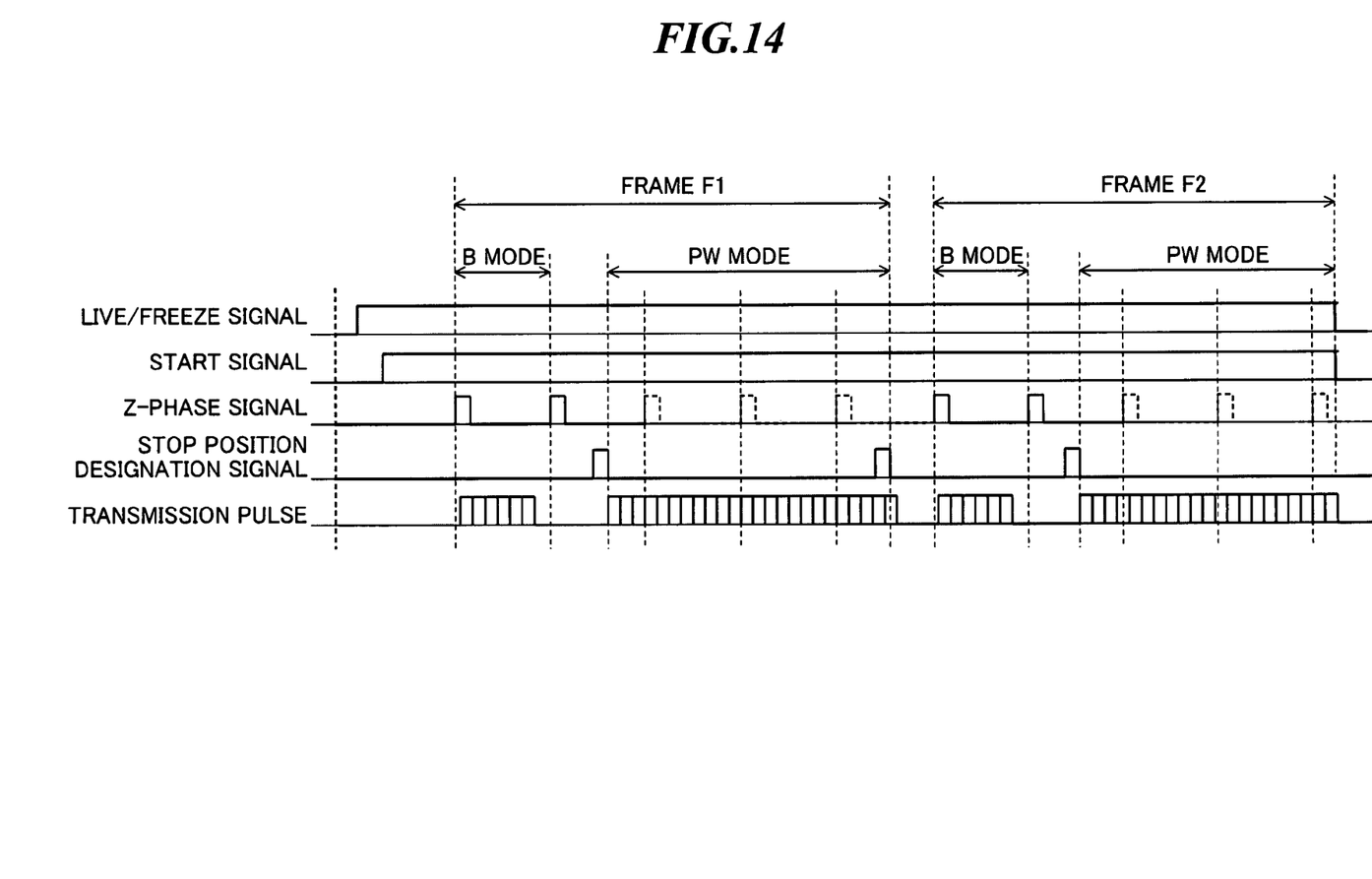
FIG. 14 is a timing chart showing an operation in PW mode of the ultrasonic diagnostic apparatus as shown in FIG. 1.

FIG. 14 is a timing chart showing an operation in PW mode of the ultrasonic diagnostic apparatus as shown in FIG. 1. In this example, B-mode imaging and PW-mode imaging are alternately performed. The control unit 27 sets the live mode by activating the live/freeze signal to the high level according to the operation of an operator using the console 4. Then, after a predetermined rotation lock period elapses, the motor control unit 29 activates the start signal to the high level and allows the drive motor 14 to start rotational movement.

When starting the rotational movement, the drive motor 14 generates one pulse for one rotation as a Z-phase signal. The transmitting unit 20 generates a drive signal at timings obtained by dividing the pulse period of the Z-phase signal into equal intervals, and thereby, the ultrasonic transducer 10 sequentially transmits plural transmission pulses to the object along the plural lines while rotating. Further, the ultrasonic transducer 10 sequentially receives ultrasonic echoes reflected from the object along the plural lines to output a reception signal. A complex baseband signal is generated based on the reception signal, and the B-mode image signal generating unit 25a generates a B-mode image signal based on the complex baseband signal. In the above-mentioned manner, the B-mode image signal in the frame F1 is generated.

Then, the control unit 27 outputs one pulse as a stop position designation signal to the motor control unit 29, and thereby, the motor control unit 29 allows the drive motor 14 to stop the rotational movement at the designated angle. Here, the designated angle is determined by the time from the pulse of the Z-phase signal. Thereby, the ultrasonic transducer 10 stops at the designated angle (i.e., line) $\theta 1$ (see FIG. 13), and sequentially transmits plural transmission pulses to the object along one line. Further, the ultrasonic transducer 10 sequentially receives ultrasonic echoes reflected from the object along one line to output a reception signal. A complex baseband signal is generated based on the reception signal, and the PW-mode image signal generating unit 25c generates a PW-mode image signal based on the complex baseband signal. In the above-mentioned manner, the PW-mode image signal in the frame F1 is generated.

At the end of PW mode imaging in the frame F1, the control unit 27 outputs one pulse as a stop position designation signal to the motor control unit 29, and thereby, the motor control unit 29 allows the drive motor 14 to start the rotational movement again. When starting the rotational movement, the drive motor 14 generates one pulse for one rotation as a Z-phase signal. The transmitting unit 20 generates a drive signal at timings obtained by dividing the pulse period of the Z-phase signal into equal intervals, and thereby, the ultrasonic transducer 10 sequentially transmits plural transmission pulses to the object along the plural lines while rotating. Further, the ultrasonic transducer 10 sequentially receives ultrasonic echoes reflected from the object along the plural lines to output a reception signal. A complex baseband signal is generated based on the reception signal, and the B-mode image signal generating unit 25a generates a B-mode image signal based on the complex baseband signal. In the above-mentioned manner, the B-mode image signal in the frame F2 is generated.

Further, the line selecting unit 24 selects a line having the highest correlation with the line $\theta 1$ in the frame FN from among the $\alpha$ lines in the frame F2, and uses the line as new line $\theta 1$. That is, the line selecting unit 24 selects, in the frame F2, a line corresponding to the complex baseband signal having the highest correlation with the complex baseband signal corresponding to the line $\theta 1$ selected in the frame F1, and memorizes the line number. Thereby, even when the object rotates relative to the ultrasonic probe 1, the region of interest of the object can be tracked.

Alternatively, the line selecting unit 24 may compare phase information in the complex baseband signal generated based on the ultrasonic echoes received along the plural lines from a predetermined depth within the object when the ultrasonic transducer 10 rotates, and thereby, select a line closest in a phase to the line $\theta 1$ in the frame F1 from among a lines in the frame F2, and uses the line as new line $\theta 1$. That is, the line selecting unit 24 selects, in the frame F2, a line corresponding to the complex baseband signal closest in a phase to the complex baseband signal corresponding to the line $\theta 1$ selected in the frame F1, and memorizes the line number.

Then, the control unit 27 outputs one pulse as a stop position designation signal to the motor control unit 29, and thereby, the motor control unit 29 allows the drive motor 14 to stop the rotational movement at the designated angle. Here, the designated angle corresponds to the line selected by the line selecting unit 24 in the frame F2. Thereby, the ultrasonic transducer 10 stops at the designated angle, and sequentially transmits plural transmission pulses to the object along one line. Further, the ultrasonic transducer 10 sequentially receives ultrasonic echoes reflected from the object along one line to output a reception signal. A complex baseband signal is generated based on the reception signal, and the PW-mode image signal generating unit 25c generates a PW-mode image signal based on the complex baseband signal. In the above-mentioned manner, the PW-mode image signal in the frame F2 is generated.

By repeating the operation, the PW-mode image signal can be generated while the B-mode image signal is generated. Alternatively, only the PW-mode image signal may be generated without generating the B-mode image signal when the ultrasonic transducer 10 is stopped at the angle corresponding to the line selected by the line selecting unit 24.

The invention claimed is:

1. An ultrasonic diagnostic apparatus using an ultrasonic probe of a mechanical radial scanning type for intracavity observation and including an ultrasonic transducer for transmitting ultrasonic waves and receiving ultrasonic echoes, said apparatus comprising:

a signal processing unit configured to perform one of orthogonal detection processing and orthogonal sampling processing on a reception signal outputted from said ultrasonic transducer to generate a complex baseband signal having an in-phase component and a quadrature phase component;

a memory configured to store the complex baseband signal for at least two frames, each frame of the complex baseband signal being generated based on the ultrasonic echoes received along plural lines in respective one rotation of said ultrasonic transducer;

a line selecting unit configured to select one line from among plural lines in each frame based on the complex baseband signal stored in said memory; and an image signal generating unit configured to generate an image signal representing information on blood flow based on the complex baseband signal with reference to the line selected in each frame by said line selecting unit, wherein said line selecting unit is configured to select a line in a first frame and selects, in a second frame subsequent to the first frame, a line corresponding to the complex baseband signal having a highest correlation with the complex baseband signal corresponding to the line selected in the first frame by calculating correlation coefficients of the in-phase components and correlation coefficients of the quadrature phase components between the selected line in the first frame and plural lines in the second frame.

2. The ultrasonic diagnostic apparatus according to claim 1, further comprising:
   a motor control unit configured to control a motor, which rotates said ultrasonic transducer, to thereby control a rotational speed and a stop position of said ultrasonic transducer.

3. The ultrasonic diagnostic apparatus according to claim 1, wherein said image signal generating unit generates an image signal representing a B-mode (brightness mode) image as tomographic image information on tissues within an object to be inspected, and generates an image signal representing a CF (color flow) mode image, in which information on the blood flow is displayed as a color image superimposed on the B-mode image, based on the complex baseband signal stored in said memory.

4. The ultrasonic diagnostic apparatus according to claim 1, wherein said image signal generating unit generates an image signal representing a PW (pulse wave) mode image, in which a velocity of the blood flow detected based on transmission and reception of pulse waves is displayed.

5. A signal processing program, embodied in non-transitory form on a computer readable medium, for processing a complex baseband signal having an in-phase component and a quadrature phase component and generated by performing one of orthogonal detection processing and orthogonal sampling processing on a reception signal outputted from an ultrasonic transducer for transmitting ultrasonic waves and receiving ultrasonic echoes in an ultrasonic diagnostic apparatus using an ultrasonic probe of a mechanical radial scanning type for intracavity observation, said program allowing a CPU to execute the procedures of:
   (a) selecting one line from among plural lines in each frame based on the complex baseband signal stored in a memory for at least two frames, each frame of the complex baseband signal being generated based on the ultrasonic echoes received along plural lines in respective one rotation of said ultrasonic transducer; and
   (b) generating an image signal representing information on blood flow based on the complex baseband signal with reference to the line selected in each frame at procedure (a),
   wherein step (a) including selecting a line in a first frame and selecting, in a second frame subsequent to the first frame, a line corresponding to the complex baseband signal having a highest correlation with the complex baseband signal corresponding to the line selected in the first frame by calculating correlation coefficients of the in-phase components and correlation coefficients of the quadrature phase components between the selected line in the first frame and plural lines in the second frame.

* * * * *